United States Patent [19]

Weissman

[11] 4,323,347
[45] Apr. 6, 1982

[54] DENTAL TOOL FOR USE WITH DENTAL RETAINING SPLINTS

[75] Inventor: Bernard Weissman, New York, N.Y.

[73] Assignee: IPCO Corporation, White Plains, N.Y.

[21] Appl. No.: 188,026

[22] Filed: Sep. 17, 1980

Related U.S. Application Data

[63] Continuation-in-part of Ser. No. 70,247, Aug. 27, 1979, Pat. No. 4,260,383.

[51] Int. Cl.³ .............................................. A61C 3/00
[52] U.S. Cl. .................................................... 433/141
[58] Field of Search ................. 433/141, 144; 30/130, 30/128; 24/201 R, 230, 221 K

[56] References Cited

U.S. PATENT DOCUMENTS

D. 255,772  8/1980  Johnson et al. .................. 24/221 K

Primary Examiner—Robert Peshock
Attorney, Agent, or Firm—Friedman, Goodman & Teitelbaum

[57] ABSTRACT

A dental tool for use in conjunction with a dental retaining splint, the dental tool including an elongated handle having a splint manipulating device at one end thereof which provides a spring held twist-lock clamp for the dental splint to facilitate the placing and removing of the splint from the teeth. The other end of the handle includes a splint positioning and holding device which can enter into an axial opening in the dental splint for anchoring the splint in place on a tooth in order to accurately drill holes in adjacent teeth using the dental splint as a drill guide.

8 Claims, 9 Drawing Figures

DENTAL TOOL FOR USE WITH DENTAL RETAINING SPLINTS

RELATIONSHIP TO OTHER APPLICATIONS

This application is a continuation-in-part application to Serial No. 070,247, filed Aug. 27, 1979, now U.S. Pat. No. 4,260,383 issued Apr. 7, 1981 for "Dental Retaining Splint".

BACKGROUND OF THE INVENTION

This invention relates to dentistry in general, and more particularly to a dental tool for insertion and removal of a dental retaining splint, and positioning the dental retaining splint for facilitating accurate location of holes to be drilled in the teeth.

An improved dental retaining splint was described in the aforementioned parent application, Serial No. 070,247. The dental splint includes an elongated bar-like member with a number of tubular members extending therefrom. The tubular members each have axial openings extending therethrough. The splint is first temporarily held in a channel formed between adjacent teeth with the tubular members extending upwardly from the teeth. The axial openings are utilized as guides for a drill in order to form pilot holes in the teeth. The splint is then removed and the pilot holes function as lead holes for the formation of enlarged bores to receive the same tubular members therein. The splint is then repositioned so that the tubular members are disposed downwardly into the bores formed therefor. An inlay fills the channel and covers the splint in the final procedure step.

In utilizing such dental retaining splint, various manipulations are required. For example, initially when the splint is used as a drill guide, a temporary adhesive is utilized to hold the dental splint in place while the pilot holes are being drilled. However, it would be beneficial if the temporary adhesive could be eliminated and if the drill guide could nevertheless be held in place without the use of the adhesive. Additionally, even if the adhesive is used, occasionally insufficient time is provided for the adhesive to suitably harden and the drill guide may slightly shift in place. It would therefore be helpful to have a tool which could hold the drill guide in place while forming the various pilot holes, and at the same time accurately position the drill guide during the formation of the holes to be drilled.

Furthermore, each time the splint is placed on the teeth, it must be grasped and held in place. The splints are generally of small size and it becomes difficult for the dentist to manipulate them. This is especially the case with the retaining splints of the parent application, where the splints are initially used as drill guides and subsequently repositioned and used as the splint itself. The splints must therefore be placed and removed from the teeth numerous times during their use.

It would therefore be beneficial to provide a manipulating tool which can grasp the dental splint and easily place and remove it from the teeth.

Accordingly, it would be desirous to have a suitable dental tool which could be utilized as a manipulating device for placing and removing the dental retaining splint, and could also be utilized as a holding device for suitably aiding in the formation of the various pilot holes in the teeth.

SUMMARY OF THE INVENTION

Accordingly, it is an object of the present invention to provide a dental tool of the aforementioned type which can be used with the dental retaining splint described in the aforementioned parent application.

Another object of the present invention is to provide a single dental tool which can be utilized both for a splint manipulating device as well as a splint positioning and holding device.

A further object of the present invention is to provide a dental tool having an elongated handle with a splint manipulating device at one end thereof and a splint positioning and holding device at the other end thereof.

Still another object of the present invention is to provide a dental tool having a splint manipulating device which engages in an elongated slot provided in a dental retaining splint of the type described in the aforementioned parent application.

These objects are achieved in accordance with a preferred embodiment of the present invention, wherein the dental tool comprises an elongated handle with a splint manipulating device at one end thereof. The manipulating device includes an extended body portion with an elongated foot portion transversely positioned at the distal end of the body portion. The foot portion is adapted for entering into and twist locking beneath an elongated slot formed in the wall of a dental splint. A compression spring is retained on the body portion for coacting with the foot portion to hold the dental splint. The compression spring has a size greater than the elongated slot to bear against the wall of the dental splint. In this manner, with the foot portion locked beneath the elongated slot, and the spring above the elongated slot, the dental splint is held by the foot portion against the action of the spring.

The present invention further contemplates providing a splint positioning and holding device at the other end of the elongated handle for anchoring the splint in a first tooth while the splint is serving as a dental drill guide for adjacent teeth. By anchoring the splint in one tooth, the positioning and holding device facilitates in the accurate location of a hole to be drilled in the adjacent tooth.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like reference characters designate like parts.

DETAILED DESCRIPTION OF THE PREFERRED EMBODIMENTS

Figure 1:
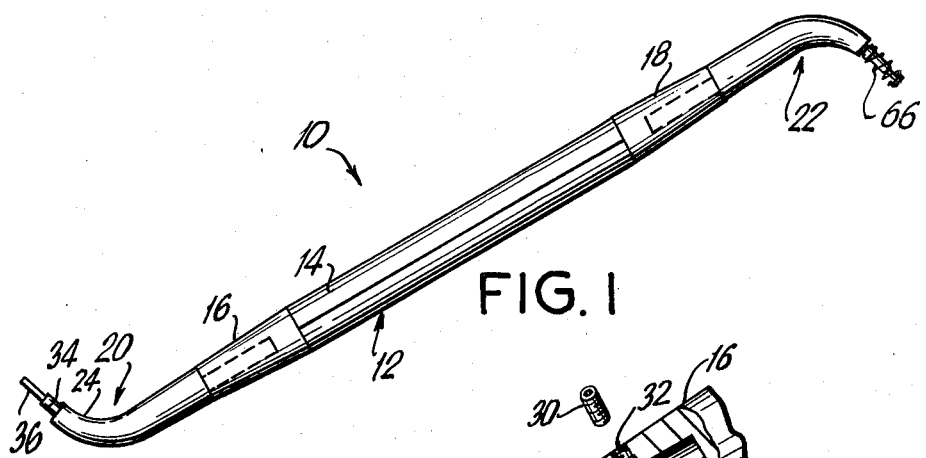
FIG. 1 is an elevational view of the dental tool in accordance with the present invention.
Figure 2:
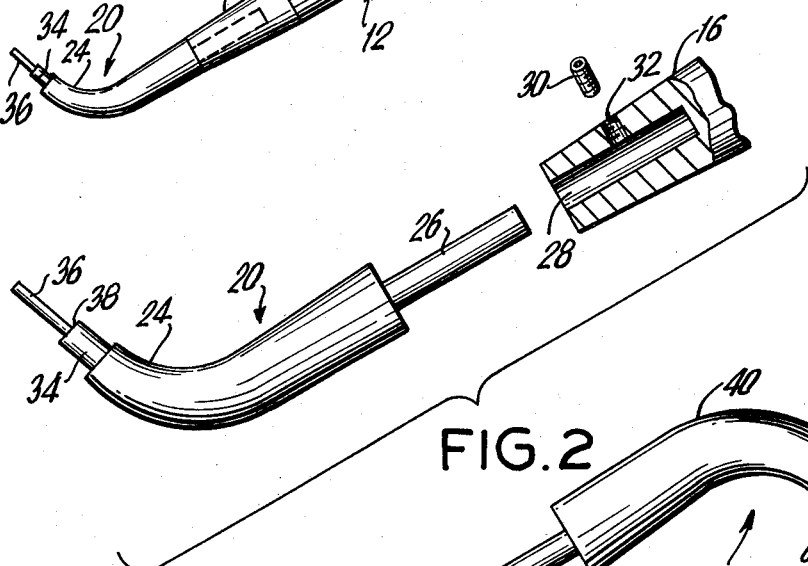
FIG. 2 is an exploded elevational view, partly broken away, showing the end of the tool having the splint positioning and holding device.
Figure 3:
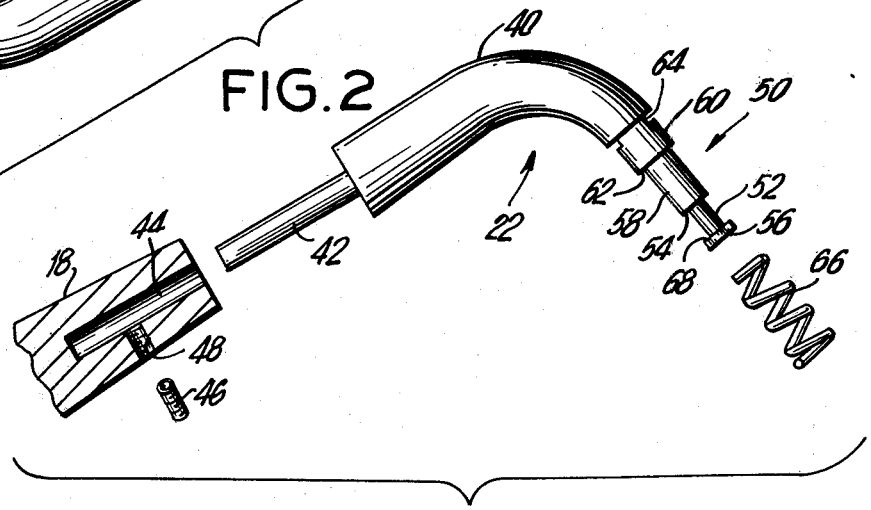
FIG. 3 is an exploded elevational view, partially broken away, showing the end of the tool having the splint manipulating device.

Referring now to FIGS. 1-3, there is shown the dental tool 10 of the present invention comprising an elongated handle 12 having a series of flats 14 formed about the periphery of the central section to facilitate grasping thereof, there preferably being four flat surfaces to define a diamond configuration in cross section. At opposing ends of the central section of the handle 12 there are provided conical end sections 16, 18. Connected to end section 16 is a splint positioning and holding device 20, while connected to the opposing end section 18 is a splint manipulating device 22.

As best shown in FIG. 2, the splint positioning and holding device 20 includes an elbow 24 having a shank 26 extending from the distal end thereof, which is received within a socket 28 formed in the conical end section 16. A set screw 30 having a socket head and cup point, locks the shank 26 in place in the socket 28 by threading into a threaded receiving hole 32 formed into the end section 16 to transversely intersect the socket 28.

Extending from the opposite end of the elbow 24 is a cylindrical post 34 from which extends a cylindrical pin 36. The pin 36 is of a smaller diameter than the post 34 with the post shoulder 38 therebetween serving as a abutment for limiting the entry of the pin 36 into a receiving hole, as will hereinafter be explained.

Referring now to FIG. 3, the splint manipulating device 22 is shown to also include an elbow 40 having a shank 42 extending from the distal end thereof, which is received within a socket 44 formed in the conical end section 18. Here again, a set screw 46 having a socket head and cup point, threads into the threaded hole 48 for locking the shank 42 in place in the socket 44, wherein the receiving hole 48 is formed into the end section 18 to transversely intersect the socket 44.

Extending from the other end of the elbow 40 is a cylindrical body portion 50 from which extends a cylindrical pin or leg 52 of smaller diameter than the body portion 50. The interconnecting surface therebetween forms a shoulder 54 which limits insertion of the leg 52 into a dental retaining splint, as will hereinafter be explained.

Figure 4:
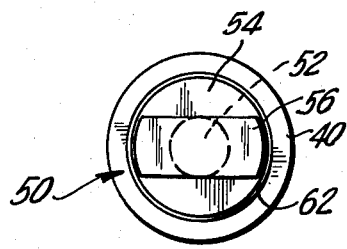
FIG. 4 is an end view of the splint manipulating device, with the elbow being partially broken away, showing the elongated foot portion without the spring being mounted on the body portion thereof.

At the distal end of the leg 52, there is provided an elongated foot 56 transversely positioned with respect to the leg 52. As can best been seen in FIGS. 3 and 4, the elongated foot 56 extends perpendicularly outwardly from opposing sides of the leg 52 which is disposed on a central portion of the foot 56.

Figure 6:
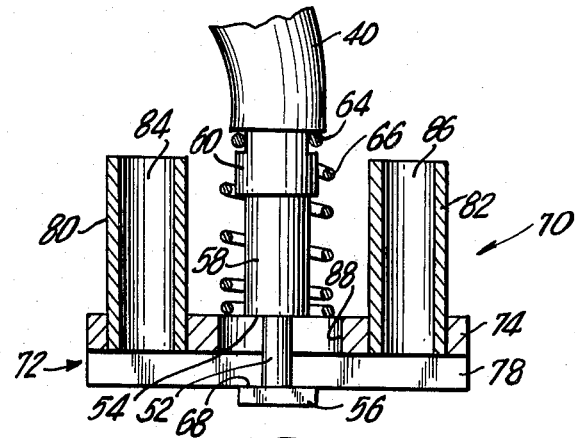
FIG. 6 is a cross sectional elevational view, partially broken away, showing the splint manipulating device being utilized with the dental retaining splint shown in FIG. 5.

The body portion 50 is itself formed of a cylindrical trunk section 58 and a cylindrical head section 60 having a larger diameter than the section 58, with the perpendicular interconnecting surface therebetween forming a shoulder 62. A reduced diameter annular neck 64 is provided at the upper end of the larger section 60 adjacent to the elbow 40. A compression spring 66 is provided along the body portion 50, extending from the elbow 40 to the upper surface 68 of the foot 56. The upper end of the spring 66 is held within the annular neck 64, as best shown in FIG. 6. It is noted, that in order to clearly show the end view of the manipulating device, the spring 66 was not shown in FIG. 4, wherein this end view shows the body portion 50 before the spring 66 is mounted thereon similar to the showing thereof in FIG. 3.

Figure 5:
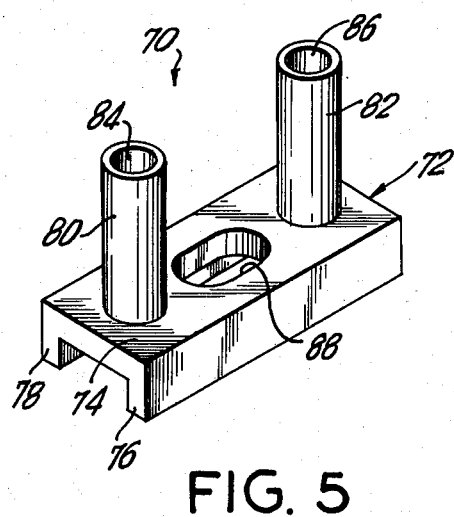
FIG. 5 is a perspective view illustrating a dental retaining splint, with which the dental tool of the present invention can be utilized.

The operation of the tool 10 can best be seen in connection with FIGS. 5-9. FIG. 5 shows a dental retaining splint 70 of the type described in the aforementioned parent application, the splint 70 including a substantially U-shaped bar-like body member 72 having a flat base wall 74 from which downwardly depends the front and rear walls 76, 78. Upwardly extending from the base wall 74 are two tubular members 80, 82 which contain axial openings 84, 86 therethrough and also through the base wall 74.

When using the dental retaining splint 70, a channel is first formed between adjacent teeth in a conventional manner well known in the dental art. The retaining splint is then placed at the bottom of the channel, usually with a layer of temporary adhesive, such as wax or other suitable material, disposed on the bottom surface of the channel to temporarily retain the splint in place. The splint is positioned with the two tubular members extending upwardly from the surface of the teeth. A pilot drill is then inserted into the axial openings 84, 86, of the tubular members 80, 82, in order to form pilot holes in the respective teeth. The retaining splint is then removed and a larger drill bit is utilized to form bores with the pilot holes functioning as lead holes for the drill bit in the formation of the bores. A layer of permanent adhesive is then placed at the bottom surface of the channel and the dental retaining splint is then positioned in the channel with the tubular members 80, 82 disposed in the respective bores. An inlay of dental restorative material is then disposed in the channel overlying the dental retaining splint to cover and complete a dental procedure.

During the course of the various above mentioned operations, it will be noted that the dental retaining splint 70 must be placed and removed from the channel at various times. In order to facilitate such placement and removal, an elongated slot 88 is formed through the base wall 74 suitably spaced between the tubular members 80, 82. The slot 88 is utilized by the tool of the present invention in order to facilitate placement and removal of the dental retaining splint 70 and similar splints.

Figure 7:
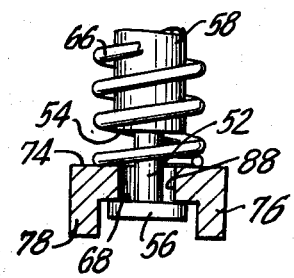
FIG. 7 is a cross section end view, partially broken away, of an operational holding step in utilizing the dental manipulating device.

Specifically, as shown in FIG. 6, the elongated foot 56 is of a size which can enter into the elongated slot 88. However, the compression spring 66 is made larger than the width of the elongated slot so that the spring cannot pass into the elongated slot, as shown in FIG. 7. Similarly, while the leg 52 can pass into the slot, the body portion 58 is of a size larger than the slot opening and cannot enter into the slot. Accordingly, the shoulder 54 serves as an abutment preventing the foot from extending too far through the slot.

The foot 56 is aligned with the elongated slot so that it can enter into the slot 88 with the compression spring 66 being restrained on the upper face of the base wall 74 as shown in FIG. 6. The tool 10, and therefore the foot 56 thereon, is then turned 90° and the downward pressure thereon is released so that the foot 56 moves upwardly and is now locked beneath the slot, as shown in FIG. 7, wherein removal of the foot is prevented. It is noted, that the spacing between the walls 76, 78 is wide enough to receive the turned foot 56 therebetween. The retaining splint, and more specifically the base wall 74 is pressed against the upper surface 68 of the foot 56 by the action of the compression spring 66. In this way, the retaining splint is sandwiched between the foot 56 and the spring 66 of the tool, and can be lifted up and removed from the tooth, or placed in a position on the tooth.

Once the retaining splint is suitably placed, the tool 10 can be easily removed from the splint by twisting or turning the tool 90° while slightly pressing down, so that the foot 56 becomes aligned with the elongated slot, as shown in FIG. 6, and can then be removed from the slot, leaving the retaining splint in place on the teeth or on any other desired surface.

Figure 9:
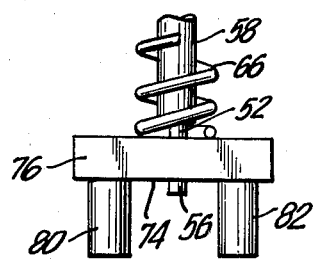
FIG. 9 is an end view, partially broken away, showing the dental manipulating device inserted in the dental retaining splint with the retaining splint being held in an opposite direction to that shown in FIGS. 6 and 7.

It should be appreciated that the foot 56 can be inserted into the elongated slot both with the tubular members extending upwardly so that in the locked position the foot 56 is disposed between the walls 76, 78 and against the base wall 74 as shown in FIGS. 6 and 7, as well as with the tubular members extending downwardly so that in the locked position the foot 56 is disposed between the tubular members 80, 82 and against the other side of the base wall 74 as shown in FIG. 9. Regardless of the positioning of the splint, the manipulating device at the end of the tool can be utilized in conjunction with the retaining splint.

Figure 8:
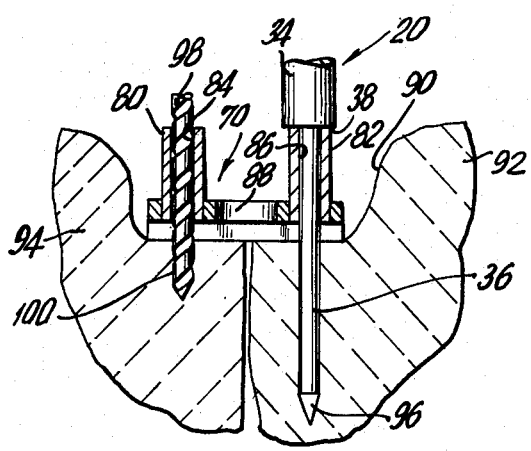
FIG. 8 is a side sectional view, partially broken away, illustrating two adjacent teeth provided with a channel which receives the dental retaining splint, and showing the splint positioning and holding device of the present invention being utilized in conjunction with the splint.

In order to utilize the positioning and holding device 20 formed at the other end of the handle, reference is made to FIG. 8. The dental retaining splint 70 is shown positioned in a channel 90 formed between adjacent teeth 92, 94. The retaining splint 70 is positioned with the tubular members extending upwardly therefrom, and a pilot first hole 96 is shown as having been drilled through the tubular member 82 by means of a drill bit 98 having passed through the axial opening 86 in the tubular member 82.

After the pilot hole 96 has been drilled, it is necessary to form a second pilot hole in the adjacent tooth 94. Accurate location of the hole requires that the retaining splint be held firmly in place. Accordingly, the splint positioning and holding device 20 is utilized as an anchor by inserting the pin 36 at the end of the handle through the tubular member 82 into the hole 96 which has been drilled in the first tooth. The shoulder 38 serves as an abutment preventing further entry of the pin into the tubular member 82. Thus, when the pin 36 passes through the axial opening 86 in the tubular member 82 and then enters into the hole 96, the pin 36 anchors the splint at that hole. The splint 70 is then suitably located so that the drill 98 can be received in the axial opening 84 in the tubular member 80 and a second pilot hole 100 can accurately be drilled in the adjacent tooth 94. It is noted, that the pin 36 permits the splint 70 to be pivoted so that the other tubular member 80 can be suitably located to provide the proper pilot holes. These pilot holes will then be used as lead holes for the formation of bores so as to receive the tubular members therein when the retaining splint is positioned in the channel in an opposite direction.

It is noted, that both the positioning and holding device 20 and the manipulating device 22 are removable from the handle 12, and can be replaced with similar devices in the dental art when required, such as when one of the devices is damaged.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental tool comprising an elongated handle with a splint manipulating device at one end thereof, said manipulating device including an extended body portion, an elongated foot portion transversely positioned at a distal end of said body portion for entering into an elongated slot provided in a wall of a dental retaining splint, said foot portion extending perpendicularly outwardly in opposite directions from said body portion so that said foot portion locks against an outer surface of the splint wall, spring means for abutting against an opposite inner surface of the splint wall to retain the splint, said spring means including a compression spring having a first end disposed on said body portion and a second opposing end extending freely towards said foot portion, said second spring end being free and resiliently movable towards and away from said foot portion, said compression spring having a size greater than said elongated foot, and said body portion including means for retaining said first end of said compression spring on said body portion, whereby with said foot portion locked beneath the elongated slot, the dental splint is sandwiched between said foot portion and second said spring end, the dental splint being held by said foot portion against the resilient action of said compression spring.

2. A dental tool as in claim 1, wherein said body portion means includes an annular neck of reduced thickness provided in said body portion in spaced relationship from said foot portion for fixedly receiving therein said first end of said compression spring.

3. A dental tool as in claim 1, wherein said body portion includes an elongated trunk portion of a selected size for preventing passage thereof through the elongated slot, and an elongated leg portion interconnecting said trunk and foot portions, said leg portion having a selected size smaller than said trunk portion for permitting passage thereof through the elongated slot, a trunk shoulder provided between said leg and trunk portions operating as a stop member to limit entry of said manipulating device into the elongated slot.

4. A dental tool as in claim 3, wherein said body portion means includes an annular neck of reduced thickness provided in said trunk portion for fixedly receiving therein said first end of said compression spring.

5. A dental tool as in claim 1, and further comprising a splint positioning and holding device at the opposite end of said elongated handle, said splint positioning and holding device including means for anchoring the dental retaining splint in a tooth, said splint positioning and holding device means including a cylindrical pin extending from a larger sized cylindrical post, a shoulder being provided between said post and said pin to operate as a stop member to limit entry of said pin into the dental retaining splint.

6. A dental tool as in claim 5, and further comprising elbow means respectively connecting said manipulating device in an approximate right angle relationship with said handle, and said positioning and holding device in an approximate right angle relationship with said handle, and wherein said manipulating device and said positioning and holding device face in opposing directions.

7. A dental tool as in claim 5, and further comprising coupling means for releasably coupling both said manipulating device and said positioning and hold device to said handle.

8. A dental tool as in claim 7, wherein said coupling means comprises a shank portion respectively provided at an end of each of said devices, a socket provided at each end of said elongated handle for respectively receiving said shank portion of an associated one of said devices, and a set screw for each of said devices being received at each end of said handle and being disposed transversely to each of said sockets for respectively clamping each of said shank portions to said handle.

* * * * *